United States Patent
Park et al.

[11] Patent Number: 5,900,810
[45] Date of Patent: May 4, 1999

[54] CAPACITIVE SENSOR ASSEMBLY

[75] Inventors: Kyong M Park, Thousand Oaks; Phuoc Vinh Le, Anaheim; Marcos A. Nassar, Los Angeles, all of Calif.

[73] Assignee: Kavlico Corporation, Moorpark, Calif.

[21] Appl. No.: 08/767,808

[22] Filed: Dec. 17, 1996

[51] Int. Cl.⁶ .................................................. B60Q 1/00
[52] U.S. Cl. ...................... 340/450.3; 340/439; 340/440; 340/459; 340/618; 340/689; 340/693.5; 33/366; 73/53.05; 73/304 C; 123/196 M; 123/196 S; 180/282; 324/663; 324/698
[58] Field of Search ..................................... 340/438, 439, 340/440, 450.3, 459, 460, 612, 618, 689, 693.5; 33/366; 123/196 R, 196 CP, 196 M, 196 S, 198 D; 324/71.1, 441, 439, 324, 663, 664, 665, 689, 698; 73/53.05, 61.74, 117.3, 295, 304 R, 304 C; 180/271, 277, 279, 282

[56] References Cited

U.S. PATENT DOCUMENTS

| | | | |
|---|---|---|---|
| 3,882,967 | 5/1975 | Gulla et al. | 73/295 |
| 3,946,494 | 3/1976 | Wells | 33/366 |
| 3,992,951 | 11/1976 | Erspamer et al. | 73/497 |
| 4,409,832 | 10/1983 | Konjedic | 73/292 |
| 4,422,243 | 12/1983 | Brunson et al. | 33/366 |
| 4,521,973 | 6/1985 | Wiklund et al. | 33/366 |
| 4,641,434 | 2/1987 | Engler | 33/366 |
| 4,644,662 | 2/1987 | Anderson et al. | 33/366 |
| 4,646,070 | 2/1987 | Yasuhara et al. | 340/603 |
| 4,706,193 | 11/1987 | Imajo et al. | 340/438 |
| 4,707,927 | 11/1987 | Hiyama | 33/366 |
| 4,811,491 | 3/1989 | Phillips et al. | 33/366 |
| 4,846,954 | 7/1989 | Ryan et al. | 33/366 |
| 4,912,662 | 3/1990 | Butler et al. | 364/559 |
| 4,924,702 | 5/1990 | Park | 73/304 |
| 4,981,039 | 1/1991 | Hayashi et al. | 73/292 |
| 5,083,383 | 1/1992 | Heger | 33/366 |
| 5,159,313 | 10/1992 | Kawai et al. | 340/450.3 |
| 5,170,567 | 12/1992 | Davis et al. | 33/366 |
| 5,233,875 | 8/1993 | Obermeier et al. | 73/718 |
| 5,237,753 | 8/1993 | Carlson et al. | 33/366 |
| 5,261,279 | 11/1993 | Wolf et al. | 73/517 R |
| 5,299,456 | 4/1994 | Steiner | 73/308 |
| 5,335,190 | 8/1994 | Nagle et al. | 364/571.01 |
| 5,382,942 | 1/1995 | Raffa et al. | 340/438 |
| 5,469,632 | 11/1995 | Boenning | 33/366 |
| 5,479,716 | 1/1996 | Murphy | 33/366 |
| 5,540,086 | 7/1996 | Park et al. | 73/53.05 |

*Primary Examiner*—Daniel J. Wu
*Attorney, Agent, or Firm*—Oppenheimer Wolff & Donnelly LLP

[57] ABSTRACT

A sensor assembly includes a tilt sensor, an oil level sensor, an oil temperature sensor and an oil deterioration sensor, as well as associated output signal conditioning electronics integrated within a common assembly. The sensor assembly is configured to receive a volume of motor oil proportional to a total volume of oil in an engine. The oil level sensor, oil temperature sensor and oil deterioration sensors include electrodes which are completely or partially immersed in the volume of motor oil depending upon the total volume of oil in the engine. The tilt sensor includes only two electrodes both of which are at least partially immersed within a controlled volume of dielectric fluid which is physically and electrically isolated from the volume of motor oil. One of the electrodes of the tilt sensor is completely immersed in the controlled volume of dielectric fluid independent of an angle of the tilt sensor relative to a vector representing forces such as gravity applied to the tilt sensor.

16 Claims, 6 Drawing Sheets

CAPACITIVE SENSOR ASSEMBLY

BACKGROUND OF THE INVENTION

1. Field of the Invention

The present invention relates to a capacitive sensor assembly and, in one embodiment pertains to a multifunctional sensor assembly including at least a tilt sensor and, optionally, one or several of an oil level sensor, an oil temperature sensor and an oil deterioration sensor, as well as signal conditioning electronics.

2. Description of the Related Art

Today's luxury automobiles rely heavily upon control systems which receive input signals from a wide variety of sensing devices. To ensure proper functioning of these control systems, a large number of highly dependable and accurate electronic transducers are needed to provide the aforementioned input signals. However, the implementation of too many transducers has proven to be uneconomical for automobile manufacturers. Thus, there is a need for a multifunctional sensor assembly including a plurality of transducers and their associated signal conditioning electronics and an object of the present invention is to provide the same.

SUMMARY OF THE INVENTION

In accordance with a specific illustrative embodiment of the present invention, a multifunctional sensor assembly for measuring characteristics of motor oil in a vehicle includes a housing, a plurality of sensors positioned within the housing and a tilt sensor mechanically coupled to the housing. The housing is mechanically coupled to a vehicle in a substantially fixed orientation relative to the vehicle. The housing is formed and positioned relative to other components of the vehicle to receive a volume of motor oil proportionally related to a total volume of motor oil in the vehicle. The plurality of sensors are adapted to measure characteristics of the motor oil. The tilt sensor provides an output signal indicative of an orientation of the tilt sensor relative to a vector representing forces applied to the tilt sensor.

In another aspect of the present invention, the sensor assembly includes a housing mechanically coupled to a vehicle in a substantially fixed orientation relative to the vehicle and a plurality of sensors. The housing includes a chamber for receiving motor oil of the vehicle. The chamber is formed and positioned relative to other components of the vehicle such that a volume of the motor oil proportionally related to a total volume of motor oil in the vehicle is provided to the chamber. The plurality of sensors are suitable positioned within the housing to measure characteristics of the motor oil.

In a further aspect of the present invention, the plurality of sensors include an oil level sensor, an oil temperature sensor and an oil deterioration sensor.

In another aspect of the present invention, the sensor assembly includes a housing mechanically coupled to a vehicle in a substantially fixed orientation relative to the vehicle and a tilt sensor mechanically coupled to the housing. The tilt sensor is adapted to provide an output signal indicative of an orientation of the tilt sensor relative to a vector representing forces applied to the tilt sensor. The tilt sensor includes a reservoir partially formed by an electrode substrate. The tilt sensor further includes a dielectric fluid within the reservoir. The electrode substrate includes only two electrodes, tilt measurement and reference electrodes. The electrode substrate is constructed and a volume of the dielectric fluid is selected such that the tilt reference electrode is completely covered by the dielectric fluid and the tilt measurement electrode is only partially covered by the dielectric fluid independent of the orientation of the tilt sensor relative to the vector.

In another aspect of the present invention, the sensor assembly includes a plurality of chambers interconnected to form a single housing and a plurality of sensors mechanically coupled to the chambers. At least one of the chambers receives motor oil of the vehicle. The sensors are adapted to measure characteristics of the motor oil.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein.

DETAILED DESCRIPTION OF THE PREFERRED EMBODIMENTS

Figures 1, 2:
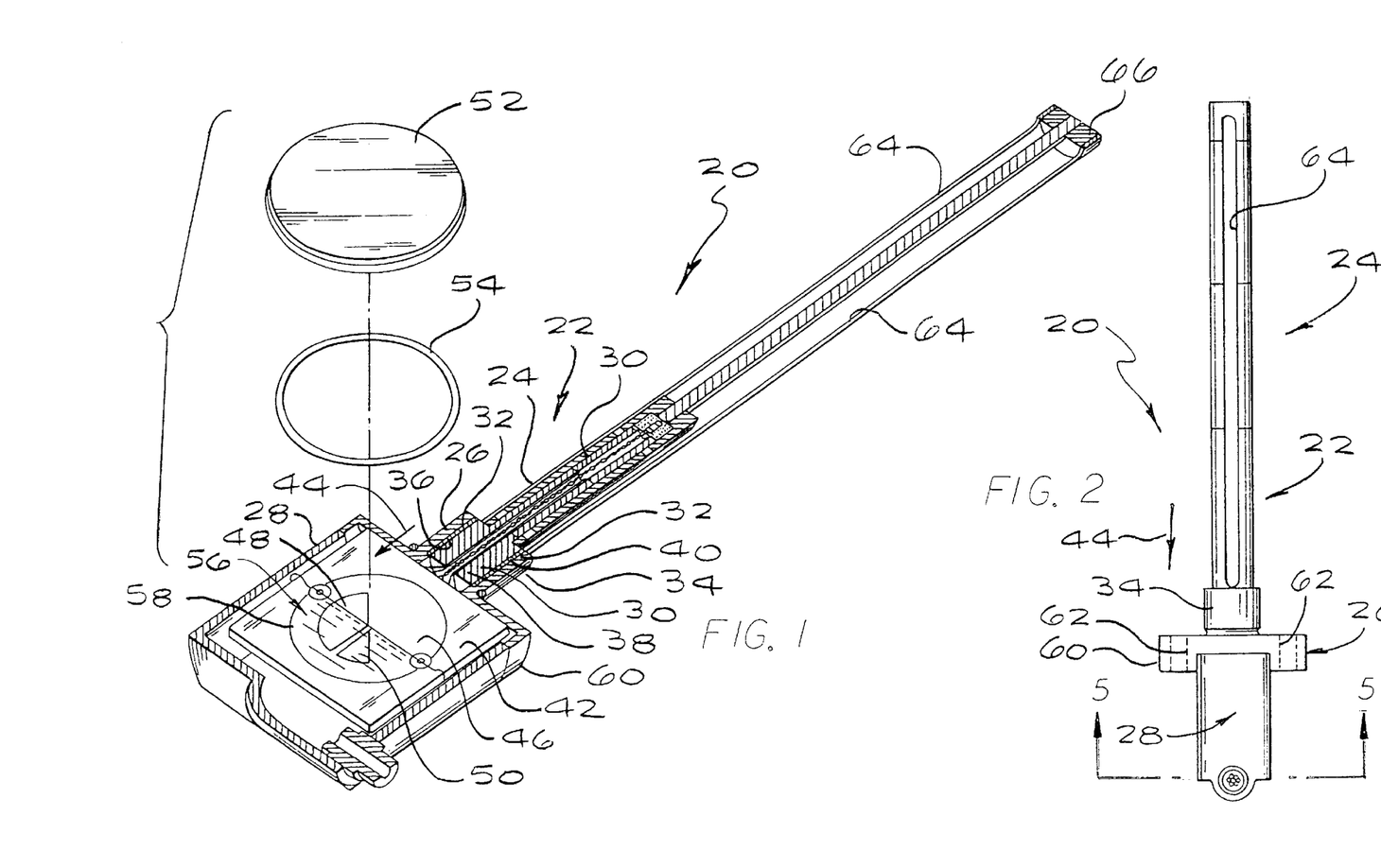
FIG. 1 is a cross-sectional perspective view of an exemplary preferred multifunctional sensor assembly according to the present invention; the view additionally includes an exploded view of a tilt sensor assembly of the multifunctional sensor assembly.
FIG. 2 is a side view of the multifunctional sensor assembly of FIG. 1.

As shown in FIG. 1, an exemplary multifunctional sensor assembly 20 includes a housing 22 which, in turn, includes an upper housing portion 24, an intermediate housing portion 26 and a lower housing portion 28. The sensor assembly 20 also includes an electrode support structure 30; and the upper housing portion further includes a sleeve portion 32.

In the illustrated preferred embodiment, the intermediate housing portion 26 includes a collar portion 34 with a substantially cylindrical inner surface 36. The electrode support structure 30 preferably includes a lower portion 38 with a substantially cylindrical outer surface 40. The sleeve portion 32 is preferably cylindrical in shape and sized to receive the electrode support structure 30 into the upper housing portion 24 with the outer surface 40 fitting snugly against the inside surface of the sleeve portion 32. In similar fashion, the inner surface 36 of the collar portion 34 is complementary to the outer surface of the sleeve portion 32 and sized such that the sleeve portion 32 fits snugly within the intermediate housing portion 26 when the sensor assembly 20 is fully assembled.

The multifunctional sensor assembly 20 measures characteristics of motor oil in a vehicle (e.g., oil level, oil temperature and oil deterioration) as well as an angular position of a tilt sensor assembly 42 relative to a vector 44 representing a vector sum of forces applied to the tilt sensor assembly 42. When the vehicle is not in motion, the aforementioned forces predominantly comprise gravity.

Figures 5, 10:
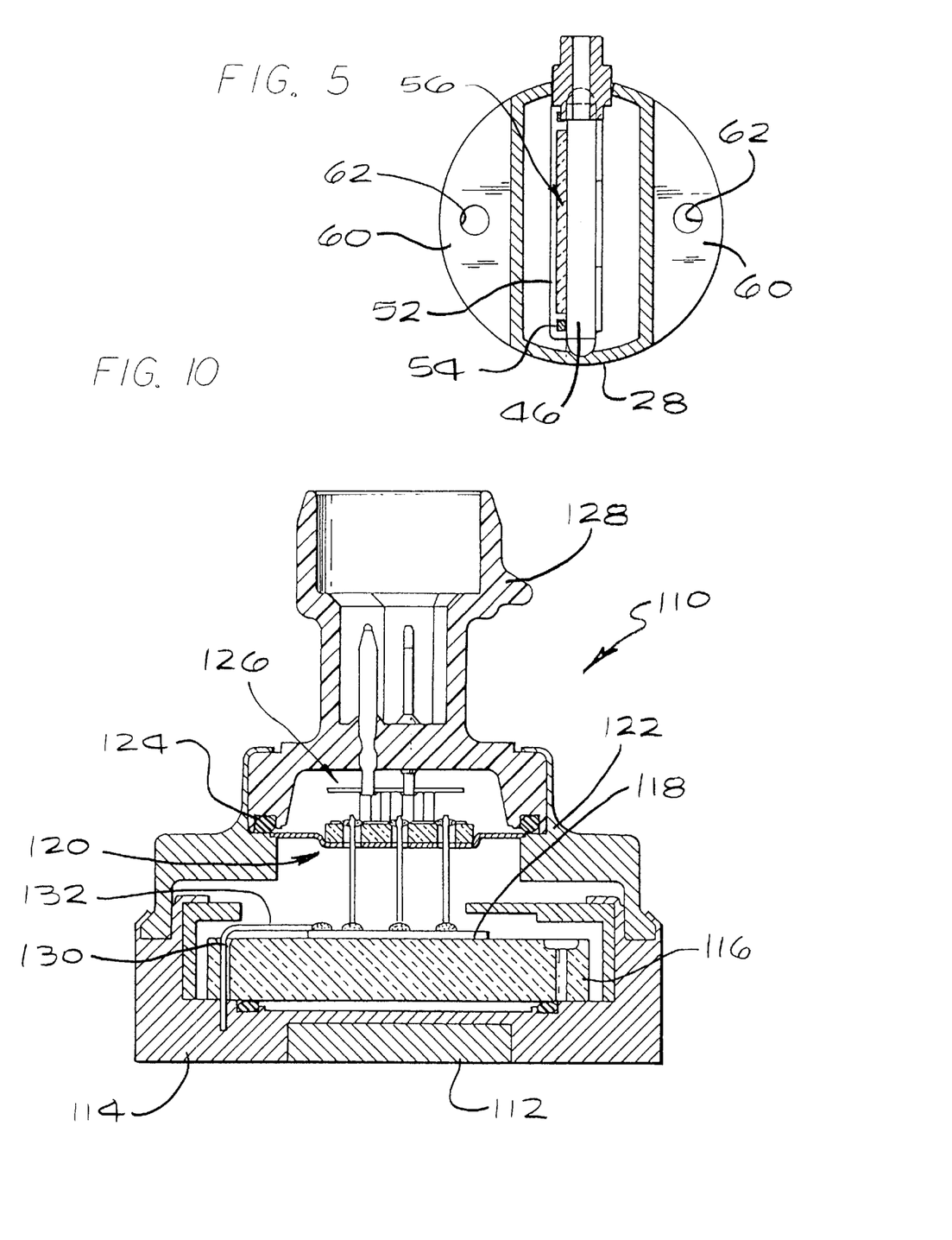
FIG. 5 is a cross-sectional end view of the multifunctional sensor assembly along lines 1—1 of FIG. 2.
FIG. 10 is an alternative preferred embodiment of the sensor assembly which includes the tilt sensor assembly of FIG. 1 and tilt sensor output signal conditioning electronics.

The tilt sensor assembly 42 includes an electrode substrate 46 upon which a thin conductive material is coated to form a measuring electrode 48 and a reference electrode 50. An exemplary electrode substrate 46 comprises a ceramic material. The tilt sensor assembly 42 also includes a ground plate 52 and a gasket 54 which are shown in FIG. 1 in an exploded view. The ground plate 52 is secured to the electrode substrate 46 at a predetermined distance from the electrodes 48, 50 (FIG. 5, also). The gasket 54 is fitted between the ground plate 52 and the electrode substrate 46 to provide a reservoir 56 within which a predetermined or controlled volume of a dielectric fluid 58 is provided. An exemplary dielectric fluid 58 comprises a silicone fluid or other nonvolatile fluid which is of an appropriate viscosity to operate at high temperatures.

During assembly, the tilt sensor assembly 42 is positioned within the lower housing portion 28. Thereafter, the intermediate housing portion 26 is welded to or secured to the lower housing portion 28 in some other conventional manner. The electrode substrate 46 is constructed, the tilt sensor assembly 42 is positioned within the lower housing portion 28 and the volume of the dielectric fluid 58 is selected such that the reference electrode 50 is completely covered by the dielectric fluid 58, independent of the orientation of the tilt sensor assembly 42 relative to the vector 44. The complete immersion of the reference electrode 50, as stated above, presupposes that the vehicle will be operated in a conventional fashion, e.g., with all of its wheels in contact with the driving surface.

The intermediate housing portion 26 further includes a flange portion 60, as best shown in FIG. 2. The flange portion 60 includes means for securing the sensor assembly 20 to a vehicle. Such securing means can, for example, comprise apertures 62 which are bored through the flange portion 60. As shown in FIG. 1, the sensor assembly 20 may also include a gasket 62 which is fitted around the collar portion 34 of the intermediate housing portion 26. The gasket 62 serves to reduce vibrational contact between a mounting member of the vehicle (not shown) and the intermediate housing portion 26.

As shown in FIGS. 1 and 2, the upper housing portion 24 additionally includes flutes 64 which allow engine oil to enter into the upper housing portion 24. The upper housing portion 24 is positioned relative to other components of the vehicle (not shown) to receive a volume of motor oil proportionally related to a total volume of motor oil in the vehicle. The sensor assembly 20 also includes an end cap 66 which is sized to be fitted snugly within the upper housing portion 24. As the total volume of motor oil in the vehicle decreases, the aforementioned volume of motor oil is forced by gravity toward the collar portion 34 and, as a result, enters into the upper housing portion 24 along progressively shorter portions of the flutes 64 beginning adjacent to the collar portion 34 and continuing toward the end cap 66. As best shown in FIG. 2, an exemplary upper housing portion 24 includes two flutes 64 which are formed along substantially the entire length of the upper housing portion 24. However, the subject matter of the present invention additionally contemplates that the upper housing portion 24 may be formed with other types of openings or apertures which facilitate the ingress of engine oil as discussed above.

Figure 3:
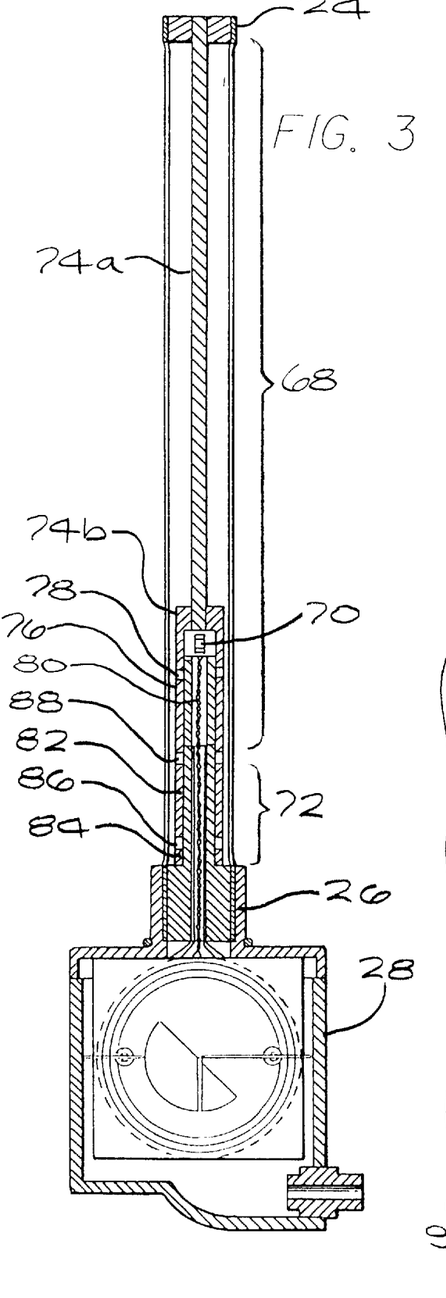
FIG. 3 is a cross-sectional front view of the multifunctional sensor assembly of FIG. 1.

Referring to FIG. 3, the illustrated exemplary embodiment of the sensor assembly 20 further includes an oil level sensor 68, a oil temperature sensor 70 and an oil deterioration sensor 72. Generally, a plurality electrodes are fitted about or otherwise supported within the upper housing portion 24 by the electrode support structure 30.

The oil level sensor 68 comprises an oil level measuring electrode 74 and an oil level reference electrode 76 which are electrically isolated from each other by an insulator 78. The illustrated exemplary oil level measuring electrode 74 includes two portions: a rod portion 74a which is fitted at one end into the end cap 66 and a retaining portion 74b which is cylindrically bored as shown to receive the oil temperature sensor 70, to fit snugly over the electrode support structure 30, and to receive the opposing end of the rod portion 74a. Thus, the end cap 66 and the retaining portion 74b secure the rod portion 74a within the upper housing portion 24. The upper housing portion 24 serves as the ground terminal for both the oil level measuring electrode 74 and the oil level reference electrode 76. As the oil level decreases, the area of the measuring electrode 74 immersed in motor oil decreases resulting in a decrease in the capacitance between the measuring electrode 74 and the upper housing portion 24. As shown in FIG. 3, the electrode support structure 30 includes vias or conduits through which electrical connections from signal conditioning circuitry are made to the electrodes 74, 76. The capacitor formed between the measuring electrode 74 and the upper housing portion 24 varies in capacitance depending upon the volume of oil in the upper housing portion 24. The capacitor formed between the reference electrode 76 and the upper housing portion 24 does not vary in capacitance provided sufficient engine oil remains to completely immerse the reference electrode 76 at all times, even when the vehicle is moving.

Figure 4:
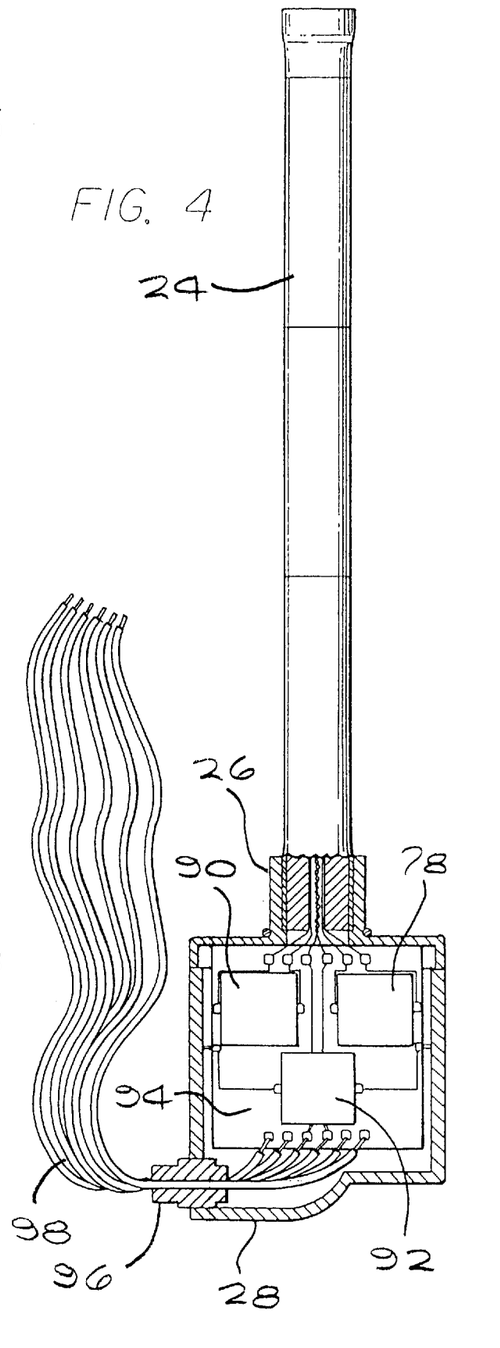
FIG. 4 is a partial cross-sectional rear view of the multifunctional sensor assembly of FIG. 1.

As best shown in FIG. 4, the exemplary sensor assembly 20 further includes an oil level sensor hybrid 78 which is electrically connected as discussed above to the capacitors formed by the electrodes 74, 76 and the upper housing portion 24. The oil level sensor hybrid 78 generates an output voltage which is proportionally related to the ratio of the capacitance between the electrode 74 and the upper housing portion 24 to the capacitance between the electrode 76 and the upper housing portion 24. Changes in this output voltage indicate changes in the oil level within the upper housing portion 24.

Referring to FIG. 3, an exemplary oil temperature sensor 70 comprises a Sensohm resister available from the Ferro Corporation. The temperature variable resistive element is positioned sufficiently close to the oil level reference electrode 76 to remain thermally coupled to the motor oil within the upper housing portion 24, even when the oil level is very low. As may be readily appreciated, the oil temperature sensor 70 can include alternative circuit elements whose electrical characteristics vary with changes in temperature.

The oil temperature sensor 70 generates an output voltage which is proportionally related to the temperature of the motor oil within the upper housing portion 24. The electrode support structure 30 is preferably formed with an inner channel 80 through which electrical connections from the plurality of electrodes are routed.

The oil deterioration sensor 72 illustrated in FIG. 3 comprises an oil deterioration measuring electrode 82 and an oil deterioration reference electrode 84 which are electrically isolated from each other by an insulator 86. The oil level reference electrode 76 and the oil deterioration measuring electrode 82 are electrically isolated from each other by an insulator 88. The upper housing portion 24 serves as a ground terminal for both the oil deterioration measuring electrode 82 and the oil deterioration reference electrode 84. The motor oil is a dielectric material and, because it circulates freely between the electrodes 82, 84 and the upper housing portion 24, forms two capacitors; a first capacitor between the oil deterioration measuring electrode 82 and the upper housing portion 24 and second capacitor between the oil deterioration reference electrode 84 and the upper housing portion 24. As the quality of the oil changes, e.g., deteriorates, the dielectric constant of the oil changes. The capacitor formed between the measuring electrode 82 and the upper housing portion 24 varies in capacitance depending upon the quality of the oil within the upper housing portion 24, as does the capacitor formed between the reference electrode 84 and the upper housing portion 24. As shown in FIG. 3, the electrode support structure 30 includes vias or conduits through which electrical connections from signal conditioning circuitry are made to the electrodes 82, 84.

As shown in FIG. 4, the exemplary sensor assembly 20 further includes an oil deterioration sensor hybrid 90 which is electrically connected as discussed above to the capacitors formed by the electrodes 82, 84 and the upper housing portion 24. The oil deterioration sensor hybrid 90 generates an output voltage which is proportionally related to the capacitance between the oil deterioration measuring electrode 82 and the upper housing portion 24. Changes in this output voltage indicate changes in the quality of the motor oil within the upper housing portion 24. The oil deterioration sensor hybrid 90 utilizes the capacitance between the oil deterioration reference electrode 84 and the upper housing portion 24 to compensate for oil temperature fluctuations.

The exemplary sensor assembly 20 also includes a tilt sensor hybrid 92 which is electrically connected to the capacitors formed by the electrodes 48, 50 and the upper housing portion 24. Operation of the tilt sensor hybrid 92 is discussed in greater detail with reference to FIGS. 6, 7, 8A–8C and 9.

The exemplary sensor assembly 20 shown in FIG. 4 also includes a circuit board 94 upon which the hybrids 78, 90, 92 are mounted. As may be readily appreciated, a plurality of hybrid circuits mounted on a common substrate is but one way in which signal conditioning can be realized. For example, the circuitry within the hybrids 78, 90, 92 could alternatively be condensed into a single integrated circuit package. The sensor assembly 20 additionally includes a conduit 96 and output leads 98. An exemplary conduit 96 is press fit or welded to the lower housing portion 28 as shown. The output leads 98 provide a means for delivering the conditioned output signals generated by the hybrids 78, 90, 92 and the oil temperature sensor 70 and, accordingly, are routed through the conduit 96.

FIG. 5 is a cross-sectional end view of the multifunctional sensor assembly 20 along lines 1—1 of FIG. 2 and best illustrates the mechanical interface between the electrode substrate 46, the ground plate 52 and the gasket 54, as well as the reservoir 56 formed thereby.

Figure 6:
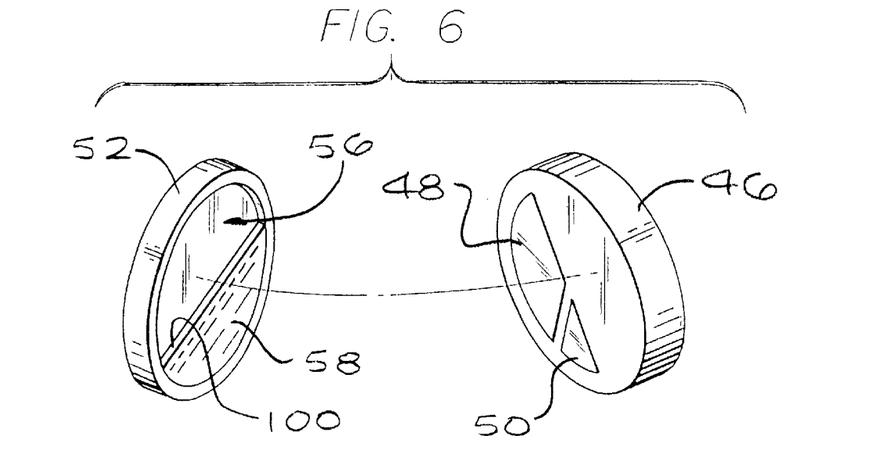
FIG. 6 shows perspective views of an electrode substrate and a ground plate of the tilt sensor assembly of FIG. 1.

FIG. 6 shows perspective views of the electrode substrate 46 and the ground plate 52. In the illustrated preferred embodiment, the reservoir 56 is cylindrical in shape and a volume of the dielectric fluid 58 is selected such that one half of the reservoir 56 is filled with the dielectric fluid 58. A top surface 100 of the dielectric fluid 58 is shown along a diameter of the reservoir 56.

Figure 7:
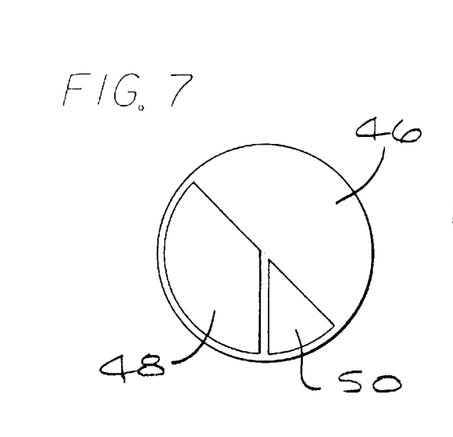
FIG. 7 is a front view of the electrode substrate of the tilt sensor assembly of FIG. 1.
Figure 8A:
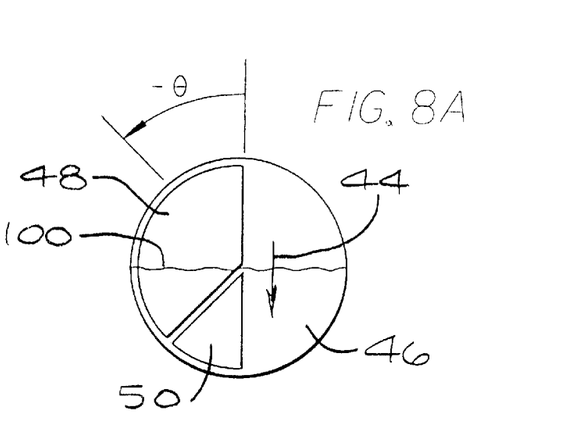
FIGS. 8A, 8B and 8C are front views of the electrode substrate and a top surface of fluid within the tilt sensor assembly of FIG. 1; the electrode substrate being shown in FIGS. 8A, 8B and 8C, respectively, at a maximum negative tilt angle, a nominal tilt angle and a maximum positive tilt angle.
Figure 8B:
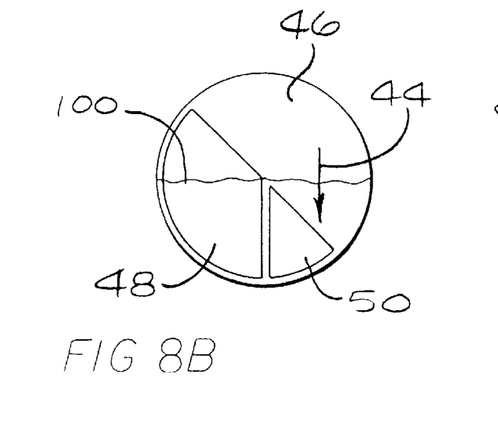
Figure 8C:
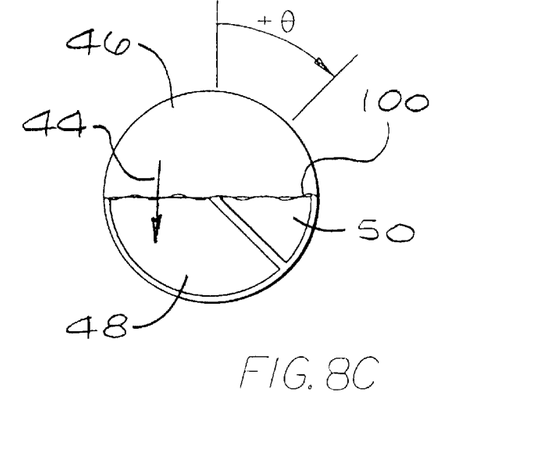

In FIG. 7, the tilt measuring electrode 48 and the tilt reference electrode 50 are shown in greater detail. As shown in FIGS. 8A–8C, the tilt sensor 42 is designed to operate within an anticipated angular range between $-\Theta$ and $+\Theta$. The reference electrode 50 is sized and positioned on the electrode substrate 46 such that it will always be immersed by the dielectric fluid 58, provided the tilt sensor assembly 20 is operating within the anticipated angular range. The measuring electrode 48 is sized and positioned on the electrode substrate 46 such that a submerged portion of the electrode 48, the ground plate 52 and the dielectric fluid 58 therebetween form a capacitor. Similarly, a capacitor is formed by the reference electrode 50, the ground plate 52 and the dielectric fluid 58 therebetween. The capacitances of the aforementioned capacitors are proportionally effected by changes in temperature. Accordingly, the latter capacitor is employed by the tilt sensor hybrid 92 to provide temperature compensation.

For purposes of the following equation, $C_\Theta$ represents the capacitance between the tilt measuring electrode 48 and the ground plate 52 and $C_r$ represents the capacitance between the tilt reference electrode 50 and the ground plate 52. The tilt sensor hybrid 92 generates an output voltage, $$V_O (C_\Theta - C_r)/(C_\Theta + C_r).$$

FIG. 8A shows the electrode substrate 46 at the maximum negative tilt angle $-\Theta$. To avoid electrical instability, the electrodes 48, 50 are preferably applied to the electrode substrate 46 such that the immersed portion of the tilt measuring electrode 48 is slightly larger than the total area of the tilt reference electrode 50 at the maximum negative tilt angle $-\Theta$. FIG. 8B shows the electrode substrate 46 at a nominal tilt angle, such as when the vehicle is parked on a surface perpendicular to the vector 44. FIG. 8C shows the electrode substrate 46 at the maximum positive tilt angle $+\Theta$.

Figure 9:
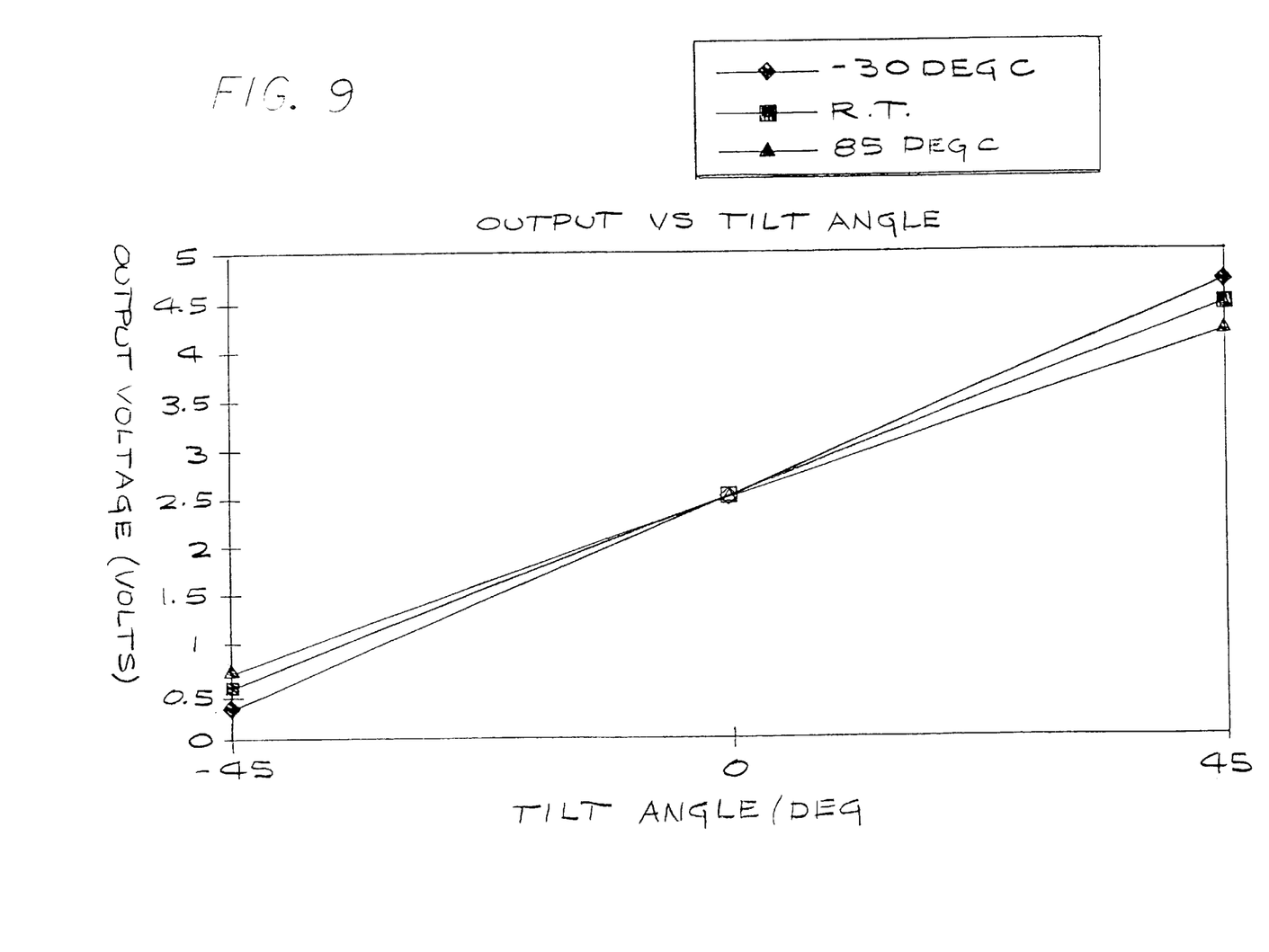
FIG. 9 shows plots of output voltages generated by output electronics of the tilt sensor assembly of FIG. 1 as a function of tilt angle at −30° C., room temperature and 85° C.

FIG. 9 shows plots of the output voltage $V_O$ generated by the tilt sensor hybrid 92 as a function of tilt angle at $-30°$ C., $23°$ C. (room temperature) and $85°$ C. The electronics within the tilt sensor hybrid 92 were trimmed to generate $V_O$ at 0.5 volts at a tilt angle of $-45°$, 2.5 volts at a tilt angle of $0°$, and 4.5 volts at a tilt angle of $+45°$. The following table sets forth the data point (in units of volts) plotted in FIG. 9.

| TILT ANGLE (DEGREES) | $-30°$ C. | R.T. | $85°$ C. |
| --- | --- | --- | --- |
| −45 | 0.321 | 0.527 | 0.590 |
| 0 | 2.459 | 2.497 | 2.445 |
| 45 | 4.670 | 4.425 | 4.177 |

FIG. 10 shows an alternative sensor assembly 110 which includes a mounting bracket 112, a rear housing 114, an electrode substrate 116, a hybrid assembly 118, an assembly of feed-through capacitors and supporting plate 120, a front housing 122, an O-ring gasket 124, an assembly of output terminals and flexible connecting strip 126 and a connector 128 assembled as shown. The electrode substrate 116 is substantially identical to the electrode substrate 46, but also includes a via 130 through which an electrical connection 132 is made between the hybrid assembly 118 and the rear housing 114 which serves as electrical ground. The hybrid assembly 118 is attached to one side of the electrode substrate 116 while tilt measuring and reference electrodes (not shown) are positioned on the opposing side.

Figure 11:
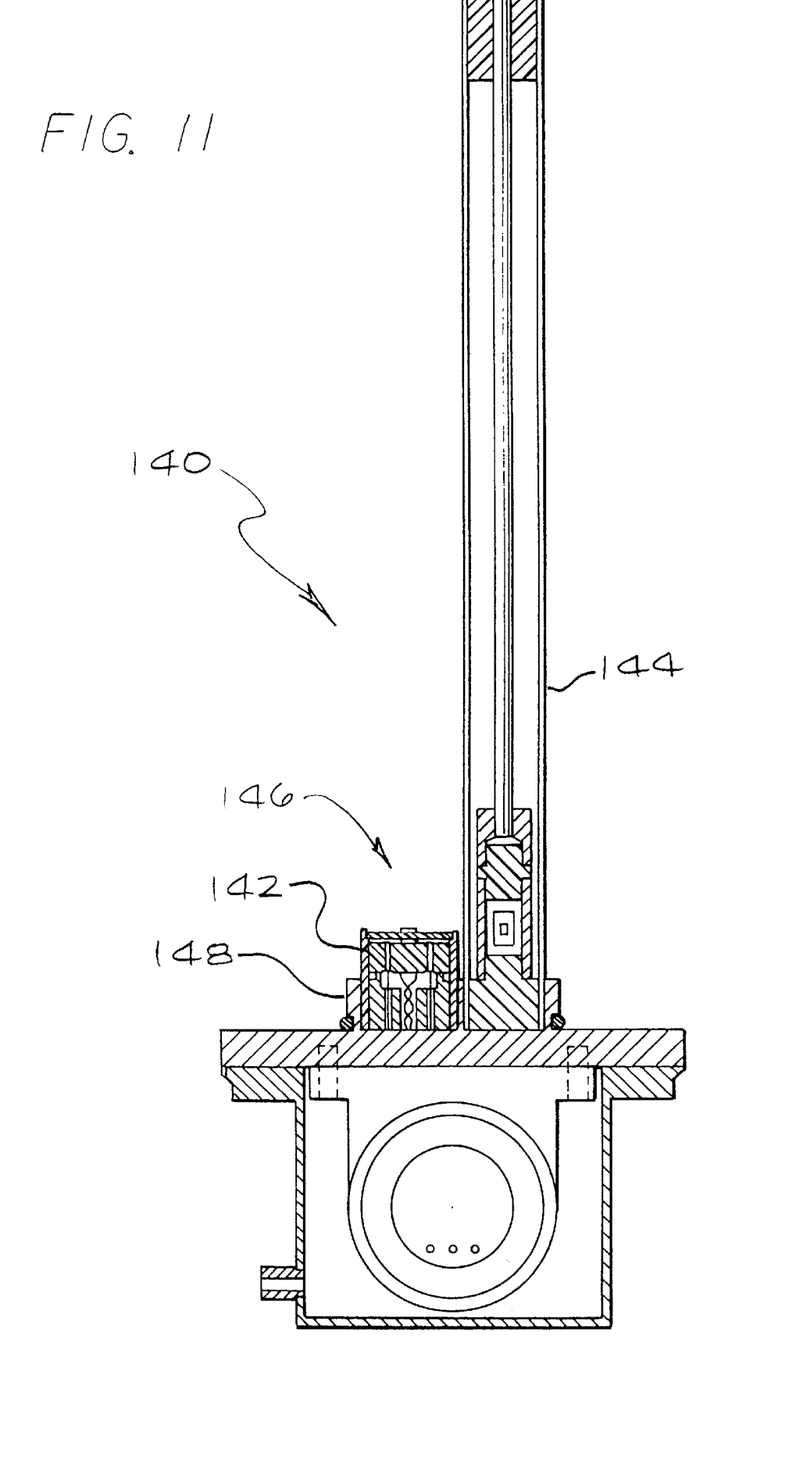
FIG. 11 is an alternative preferred embodiment of the multifunctional sensor assembly of FIG. 1, the alternative embodiment being of reduced overall length and including a repositioned oil deterioration sensor assembly of alternative design.

FIG. 11 illustrates an alternative multifunctional sensor assembly 140 which includes an oil deterioration sensor 142 positioned outside the upper housing portion 144 and directly exposed to a volume of motor oil 146. An exemplary oil deterioration sensor 142 comprises the oil deterioration sensor disclosed in U.S. Pat. No. 5,540,086 to Park et al., the entirety of which is incorporated herein.

As shown in FIG. 11, an intermediate housing portion 148 is formed to receive the oil deterioration sensor 142 and the upper housing portion 144. The upper housing portion 144 is of a reduced overall length compared to the upper housing portion 24 because it does not include electrodes for an oil deterioration sensor. The remaining components of the sensor assembly 140 are substantially identical to their corresponding components in the sensor assembly 20 rendering a description of their structural and functional characteristics reiterative.

In conclusion, it is to be understood that the foregoing detailed description and the accompanying drawings illustrate the principles of the invention. However, various changes and modifications may be employed without departing from the spirit and scope of the invention. Thus, by way of example and not of limitation, the disclosed plurality of transducers could further include a pressure transducer or other sensing devices. Accordingly, the present invention is not limited to the specific form shown in the drawings and described in detail hereinabove.

What is claimed is:

1. A multifunctional sensor assembly for measuring characteristics of motor oil in a vehicle, the sensor assembly comprising:

a housing mechanically coupled to a vehicle in a substantially fixed orientation relative to the vehicle, the housing including a chamber for receiving motor oil of the vehicle, the chamber being formed and positioned relative to other components of the vehicle such that a volume of the motor oil proportionally related to a total volume of motor oil in the vehicle is provided to the chamber, the chamber including a substantially cylindrical inner wall; and a plurality of sensors positioned within the housing for measuring characteristics of the motor oil, at least one of the sensors including an electrode substantially cylindrical in shape and fitted within the chamber.

2. The multifunctional sensor assembly of claim 1 wherein the at least one of the sensors comprises one of an oil deterioration sensor and an oil level sensor.

3. A multifunctional sensor assembly for measuring characteristics of motor oil in a vehicle, the sensor assembly comprising:

a plurality of chambers interconnected to form a single housing, at least one of the chambers receiving motor oil of a vehicle; and a plurality of sensors mechanically coupled to the chambers, the sensors being adapted to measure characteristics of the motor oil.

4. The multifunctional sensor assembly of claim 3 further comprising:

a tilt sensor mechanically coupled to at least one of the plurality of chambers, the tilt sensor being adapted to provide an output signal indicative of an orientation of the tilt sensor relative to a vector representing forces applied to the tilt sensor.

5. The multifunctional sensor assembly of claim 3 wherein at least one of the sensors is only partially submerged in the motor oil.

6. The multifunctional sensor assembly of claim 3 wherein at least one of the sensors is electrically isolated from the motor oil.

7. The multifunctional sensor assembly of claim 3 wherein the sensors further comprise an oil deterioration sensor and a tilt sensor.

8. The multifunctional sensor assembly of claim 3 wherein the plurality of sensors comprise an oil deterioration sensor and an oil temperature sensor.

9. The multifunctional sensor assembly of claim 8 wherein the plurality of sensors further comprise a tilt sensor.

10. The multifunctional sensor assembly of claim 3 wherein the plurality of chambers include a first chamber formed and positioned relative to other components of the vehicle to receive a volume of motor oil proportionally related to a total volume of motor oil in the vehicle and a second chamber separated from the volume of motor oil.

11. The multifunctional sensor assembly of claim 10 wherein the plurality of sensors comprise an oil level sensor positioned within the first chamber.

12. The multifunctional sensor assembly of claim 10 wherein the plurality of sensors comprise an oil deterioration sensor which is mechanically coupled to the second chamber and positioned relative to other components of the vehicle to receive a substantially constant volume of motor oil.

13. The multifunctional sensor assembly of claim 3 wherein the plurality of sensors comprise an oil deterioration sensor and an oil level sensor.

14. The multifunctional sensor assembly of claim 13 wherein the plurality of sensors further comprise a tilt sensor.

15. The multifunctional sensor assembly of claim 13 wherein the plurality of sensors further comprise an oil temperature sensor.

16. The multifunctional sensor assembly of claim 15 wherein the plurality of sensors further comprise a tilt sensor.

\* \* \* \* \*